(12) United States Patent
Johansen et al.

(10) Patent No.: US 9,187,396 B2
(45) Date of Patent: Nov. 17, 2015

(54) COMPOSITIONS AND METHODS FOR THE TREATMENT OF GLOMERULONEPHRITIS

(71) Applicant: Avexxin AS, Trondheim (NO)

(72) Inventors: Berit Johansen, Trondheim (NO); Andrea Huwiler, Bern (CH)

(73) Assignee: Avexxin AS, Trondheim (NO)

( * ) Notice: Subject to any disclaimer, the term of this patent is extended or adjusted under 35 U.S.C. 154(b) by 0 days.

(21) Appl. No.: 14/200,238

(22) Filed: Mar. 7, 2014

(65) Prior Publication Data
US 2014/0256824 A1 Sep. 11, 2014

Related U.S. Application Data

(62) Division of application No. 12/794,367, filed on Jun. 4, 2010, now Pat. No. 8,796,251.

(30) Foreign Application Priority Data

Jun. 4, 2009 (GB) .................................. 0909643.9

(51) Int. Cl.
| | |
|---|---|
| *A01N 43/00* | (2006.01) |
| *A61K 31/33* | (2006.01) |
| *A01N 35/00* | (2006.01) |
| *A61K 31/12* | (2006.01) |
| *C07C 49/227* | (2006.01) |
| *A61K 31/121* | (2006.01) |
| *A61K 31/131* | (2006.01) |
| *A61K 31/381* | (2006.01) |
| *C07C 229/12* | (2006.01) |
| *C07C 317/44* | (2006.01) |
| *C07C 323/52* | (2006.01) |
| *C07D 333/24* | (2006.01) |
| *C07D 333/38* | (2006.01) |

(52) U.S. Cl.
CPC ............ *C07C 49/227* (2013.01); *A61K 31/121* (2013.01); *A61K 31/131* (2013.01); *A61K 31/381* (2013.01); *C07C 229/12* (2013.01); *C07C 317/44* (2013.01); *C07C 323/52* (2013.01); *C07D 333/24* (2013.01); *C07D 333/38* (2013.01)

(58) Field of Classification Search
USPC .................................................. 514/183, 675
See application file for complete search history.

(56) References Cited

U.S. PATENT DOCUMENTS

| | | |
|---|---|---|
| 4,670,465 A | 6/1987 | Guzman et al. |
| 7,687,543 B2 | 3/2010 | Johansen et al. |
| 2005/0256141 A1 | 11/2005 | Nakagawa et al. |

FOREIGN PATENT DOCUMENTS

| | | |
|---|---|---|
| EP | 0765661 A2 | 4/1997 |
| JP | 09268153 A | 10/1997 |
| WO | WO-9738688 A1 | 10/1997 |
| WO | 9942101 A1 | 8/1999 |
| WO | 0002561 A1 | 1/2000 |
| WO | 0034348 A1 | 6/2000 |
| WO | 02060535 A1 | 8/2002 |
| WO | 03063878 A1 | 8/2003 |
| WO | WO-2004082402 A2 | 9/2004 |
| WO | 2008075366 A2 | 6/2008 |
| WO | 2008075978 A2 | 6/2008 |
| WO | 2009061208 A1 | 5/2009 |

OTHER PUBLICATIONS

G. Cannon, Chapter Nineteen in Burger's Medicinal Chemistry and Drug Discovery, Fifth Edition, vol. I: Principles and Practice, Wiley-Interscience 1995, pp. 783-802.*
Huwiler et. al. (Br. J. Pharmacology (2012) 167:1691-1701).*
L. Thommesen et al: "Selective Inhibitors of Cytosolic or Secretory Phospholipase A2 Block TNF-Induced Activation of Transcription Factor Nuclear Factor-kappaB and Expression of ICAM-1", The Journal of Immunology, vol. 161, 1998, pp. 3421-3430, XP002240202 cited in the application, abstract.
S. Flock et al: "Syntheses of Some Polyunsaturated Sulfur- and Oxygen-containing Fatty Acids Related to Eicosapentaenoic and Docosahexaenoic Acids", Acta Chemica Scandinavica, vol. 53, 1999, pp. 436-445, XP001148989 abstract; p. 436, right-hand column—p. 437, left-hand column, p. 438.
S. Andersen et al: "Elevated Expression of Human Nonpancreatic Phospholipase A2 in Psoriatic Tissue", Inflammation, vol. 18, No. 1, 1994.
B. Johansen et al: "Phospholipase A2 in Psoriasis", Uhl W. Nevalainen, Buchler MW (eds): Phospholipase A2 Basic and Clinical Aspects in Inflammatory Diseases. Prog Surg. Basel, Karger, 1997, vol. 24, pp. 225-231.
D. Six et al: "The Expanding Superfamily of Phospholipase A2 Enzymes: Classification and Characterization", Biochimica et Biophysica Acta 1488 (2000) 1-19.
M. Anthonsen et al: "Functional Coupling Between Secretory and Cytosolic Phospholipase A2 Modulates Tumor Necrosis Factor-A- and Interleukin-13-Induced NF-Kb Activation", The Journal of Biological Chemistry, vol. 276, No. 32, issue of Aug. 10, pp. 30527-30536, 2001.

(Continued)

*Primary Examiner* — Marcos Sznaidman
(74) *Attorney, Agent, or Firm* — Mintz Levin Cohn Ferris Glovsky and Popeo, P.C.; Peter F. Corless; Christopher R. Cowles

(57) ABSTRACT

The invention provides compositions and methods for the treatment of glomerulonephritis. In one embodiment, the invention provides a compound of formula (I)

R-L-CO—X    (I)

(wherein R is a $C_{10-24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds;
L is a linking group forming a bridge of 1 to 5 atoms between the R group and the carbonyl CO; and
X is an electron withdrawing group) or a salt thereof for use in the treatment of glomerulonephritis.

3 Claims, 6 Drawing Sheets

(56) References Cited

OTHER PUBLICATIONS

W. Sjursen et al: "Secretory and Cytosolic Phospholipase A2 Regulate the Long-term Cytokine-induced Eicosanoid Production in Human Keratinocytes", CYTOKINE, vol. 12, No. 8 (Aug.), 2000: pp. 1189-1194.
R. Sundler et al: "Acyl-Chain Selectivity of the 85 Kda Phospholipase A2 and of the Release Process in Intact Macrophages", Biochem. J. (1994) 301, 455-458 (Printed in Great Britain) the entire document.
E. A. Lianos: "Biosynthesis and role of arachidonic acid metabolites in glomerulonephritis", Nephron. 1984;37(2):73-7.
V. Cattell: "Nitric oxide and glomerulonephritis", Kidney Int. Mar. 2002;61(3):816-21.
W. G. Couser: "Pathogenesis of glomerular damage in glomerulonephritis", Nephrol Dial Transplant. 1998;13 Suppl 1:10-5.
Y. Kurogi: "Mesangial cell proliferation inhibitors for the treatment of proliferative glomerular disease", Med Res Rev. Jan. 2003;23(1):15-31.
N. Papanikolaou: "Alteration of mercuric chloride-induced autoimmune glomerulonephritis in brown-Norway rats by herring oil, evening primrose oil and OKY-046 a selective TXA-synthetase inhibitor", Prostaglandins Leukot Med. May 1987;27(2-3):129-49.
Y. Shi et al: "Attenuation of mycotoxin-induced IgA nephropathy by eicosapentaenoic acid in the mouse: dose response and relation to Il-6 expression", J Nutr Biochem. Oct. 2006;17(10):697-706. Epub 2006 Jan 9.
L. Larsen et al: "Polyunsaturated thia- and oxa-fatty acids: incorporation into cell-lipids and their effects on arachidonic acid- and eicosanoid synthesis", Biochim Biophys Acta. Oct. 18, 1997;1348(3):346-54.
C. Albrightson et al: "Selective inhibition of 5-lipoxygenase attenuates glomerulonephritis in the rat", Kidney Int. May 1994;45(5):1301-10.
T. Hansen et al: "Syntheses of two cytotoxic polyunsaturated pyrrole metabolites of the marine sponge Mycale micracanthoxea", Tetrahedron Leters 2006 45:2809-11.
T. Katagiri et al: "Trifluoromethylated amino alcohol as chiral auxiliary for highly diastereoselective and fast Simmons-Smith cyclopropanation of allylic amine", 2006 Tetrahedron 17:1157-60.
T. Hansen et al: "Syntheses of two cytotoxic polyunsaturated pyrrole metabolites of the marine sponge Mycale micracanthoxea", Tetrahedron Leters 2006 17:1157:60.
ISA/ISR/WO cited in PCT/EP2010/003384—Mailing date Aug. 6, 2010.
Atkins (Lancet (2005) 365:1797-1806).
J.G. Cannon (Chapter Nineteen in Burger's Medicinal Chemistry and Drug Discovery, Fifth Edition, vol. I: Principles and Practice, Wiley-Interscience 1995, pp. 783-802).
Cybulsky et al. (The Journal of Biological Chemistry (2002) 277:41342-41351).
Holmeide et al. (J.C.S. Perkin Trans. 1 (2000) 2271-2276).
Kishida, Etsu et al., "Distinctive inhibitory activity of docosahexaenoic acid against sphingosine-induced apoptosis," Biochimica et Biophysica Acta, vol. 1391:401-408 (1998).
Cybulsky et al. "Complement C5b-9 Membrane Attack Complex Increases Expression of Endoplasmic Reticulum Stress Proteins in Glomerular Epithelial Cells." J. Biol. Chem. 277(2002):41342-41351.
Cybulsky et al. "Complement-Induced Phospholipase $A_2$ Activation in Experimental Membranous Nephropathy." Kidney Int. 57(2000):1052-1062.
Flock et al. "Syntheses of Some Sulfur-Containing Polyunsaturated Fatty Acids as Potential Lipoxygenase Inhibitors." Synth. Commun. 37(2007):4005-4015.
Hagiwara et al. "Eicosapentaenoic Acid Ameliorates Diabetic Nephropathy of Type 2 Diabetic KKA$^y$/Ta Mice: Involvement of MCP-1 Suppression and Decreased ERK1/s and p38 Phosphorylation." Nephrol. Dial. Transplant. 32(2006):605-615.
Hao et al. "Roles of Lipid Mediators in Kidney Injury." Semin. Nephrol. 27(2007):338-351.
Holmeide et al. "Syntheses of Some Polyunsaturated Trifluoromethyl Ketones as Potential Phospholipase $A_2$ Inhibitors." J. Chem. Soc. Perkin Trans. 1. (2000):2271-2276.
Huwiler et al. "The ?3-Polyunsaturated Fatty Acid Derivatives AVX001 and AVX002 Directly Inhibit Cytosolic Phospholipase A2 and Suppress $PGE_2$ Formation in Mesangial Cells." Brit. J. Pharmacol. 167(2012):1691-1701.
Ma et al. "12/15-Lipoxygenase Inhibitors in Diabetic Nephropathy in the Rat." Prostaglandins Leukotrienes Essential Fatty Acids. 72(2005):13-20.
Nakamura et al. "Effects of Eicosapentaenoic Acids on Oxidative Stress and Plasma Fatty Acid Composition in Patients with Lupus Nephritis." In vivo. 19(2005):879-882.
Ono et al. "Characterization of a Novel Inhibitor of Cytosolic Phospholipase $A_2\alpha$, Pyrrophenone." Biochem J. 363(2002):727-735.
Robinson et al. "Suppression of Autoimmune Disease by Dietary n-3 Fatty Acids." J. Lipid Res. 34(1993):1435-1444.

* cited by examiner

A

B

C

A

B

C

COMPOSITIONS AND METHODS FOR THE TREATMENT OF GLOMERULONEPHRITIS

CROSS-REFERENCE TO RELATED APPLICATION

This application is a divisional of application Ser. No. 12/794,367, filed Jun. 4, 2010, pending, which claims priority to United Kingdom Application No. GB0909643.9, filed 4 Jun. 2009, the entire contents of which are incorporated herein by reference.

BACKGROUND OF THE INVENTION

Glomerulonephritis, also known as glomerular nephritis, abbreviated GN, is a renal disease characterized by inflammation of the glomeruli, or small blood vessels in the kidneys. It may present with isolated hematuria and/or proteinuria or as a nephrotic syndrome, acute renal failure, or chronic renal failure. Glomerulonephritis is categorised into several different pathological patterns, which are broadly grouped into non-proliferative or proliferative types. Diagnosing the pattern of GN is important because the outcome and treatment differs in different types.

Primary causes of glomerulonephritis are those which are intrinsic to the kidney, whilst secondary causes are associated with certain infections (bacterial, viral or parasitic pathogens), drugs, systemic disorders (SLE, vasculitis) or cancers.

The glomerulus is a unique vascular network with three specialised types of cell: the endothelial cell, the mesangial cell and the visceral epithelial cell Mesangial cells (MC) serve a number of functions in the renal glomerular capillary including structural support of the capillary tuft, modulation of the glomerular hemodynamics and a phagocytic function allowing removal of macromolecules and immune complexes. The proliferation of MC is a prominent feature of glomerular disease including IgA nephropathy, membranoproliferative glomerulonephritis, lupus nephritis, and diabetic nephropathy.

Reduction of MC proliferation in glomerular disease models by treatment with, for example, a low protein diet has been shown to produce extracellular matrix expansion and glomerulosclerotic changes. MC proliferation inhibitors may therefore offer therapeutic opportunities for the treatment of proliferative glomerular disease.

Mesangial proliferative glomerulonephritis is a form of glomerulonephritis which involves inflammation at the kidney glomeruli. The mesangial cells which are a part of the glomerular capillaries increase in size giving the glomeruli a lumpy appearance. MC proliferation is inhibited by a variety of pharmacological drugs, for example inhibitors against angiotensin converting enzyme (ACE), cyclin-dependent kinases (CDK), platelet derived growth factor and others. The disorder usually causes nephritic syndrome which represents protein loss in the urine. It may be present as acute, chronic or rapidly progressive glomerulonephritis and may progress to chronic renal failure.

Conventional therapies for glomerulonephritis are inadequate, and improved methods are urgently required.

SUMMARY OF THE INVENTION

The present invention provides compositions and methods for the treatment of glomerulonephritis and related conditions. In particular, the invention provides compositions comprising certain polyunsaturated long-chain ketones for the treatment of glomerulonephritis and related diseases and in particular to ketones carrying electron withdrawing substituents alpha to the carbonyl functionality in such treatment.

Thus, viewed from one aspect the invention provides a compound of formula (I)

R-L-CO—X        (I)

wherein R is a $C_{10-24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds;

L is a linking group forming a bridge of 1 to 5 atoms between the R group and the carbonyl CO; and X is an electron withdrawing group) or a salt thereof for use in the treatment of glomerulonephritis.

Viewed from another aspect the invention provides a method of treating glomerulonephritis and related diseases comprising administering to an animal, preferably a mammal, e.g. human, an effective amount of a compound of formula (I) or a salt thereof as hereinbefore described.

Viewed from another aspect the invention provides use of a compound of formula (I) or a salt thereof as hereinbefore described for use in the manufacture of a medicament for treating glomerulonephritis and related diseases.

In one aspect, the invention generally provides a method of treating glomerulonephritis involving administering to an animal, preferably a mammal, in need thereof, e.g. human, an effective amount of a compound of formula (I)

R-L-CO—X        (I), where R is a $C_{10-24}$ unsaturated hydrocarbon group optionally interrupted by one or more heteroatoms or groups of heteroatoms selected from S, O, N, SO, $SO_2$, said hydrocarbon group containing at least 4 non-conjugated double bonds;

L is a linking group forming a bridge of 1 to 5 atoms between the R group and the carbonyl CO; and X is an electron withdrawing group) or a salt thereof.

In other embodiments, the hydrocarbon group has 5, 6, or 7 double bonds.

In another embodiment, in said hydrocarbon group no double bond is conjugated with the carbonyl group. In another embodiment, in said hydrocarbon group all double bonds are in the cis configuration. In another embodiment, in said hydrocarbon group all double bonds are in the cis configuration except the double bond nearest the carbonyl. In yet another embodiment, the R group comprises 17, 18, or 19 carbon atoms. In still other embodiments, the linking group L contains —$CH_2$—, —CH($C_{1-6}$alkyl)-, —N($C_{1-6}$alkyl)-, —NH—, —S—, —O—, —CH=CH—, —CO—, —SO—, or —$SO_2$— which can be combined with each other in any (chemically meaningful) order to form the linking group. In still another embodiment, L contains at least one heteroatom, e.g. O, S, N, or SO. In still another embodiment, the L group contains a ring, e.g.,

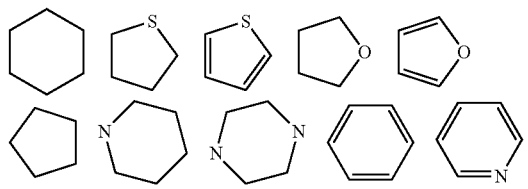

In still another embodiment, L is —NH$_2$CH$_2$, —NH(Me)CH$_2$—, —SCH$_2$—, —SOCH$_2$—, —COCH$_2$—, —CH(Me), —CH(Me)CH$_2$—, —CH(Me)-CH(Me)-, 2,4-thiophene and 2,5-thiophene.

In still another embodiment, X is O—C$_{1-6}$ alkyl, CN, OCO$_2$—C$_{1-6}$ alkyl, phenyl, CHal$_3$, CHal$_2$H, CHalH$_2$ wherein Hal represents a halogen, e.g. fluorine, chlorine, bromine or iodine, preferably fluorine. In still another embodiment, X is CHal$_3$, preferably CF$_3$.

In another embodiment, the compound of formula (I) has the formula:

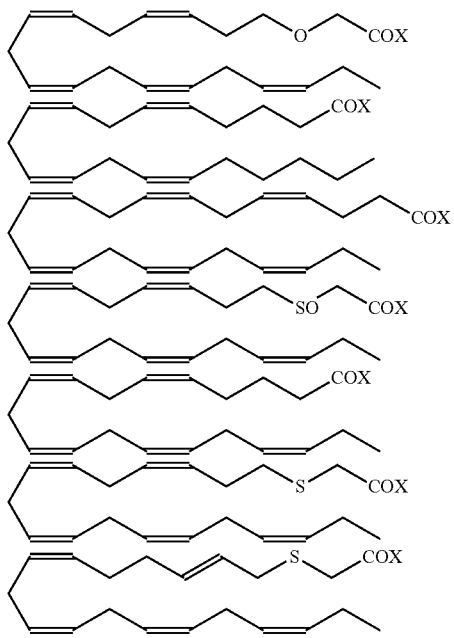

where X is as defined in an above aspect or in any other embodiment of the invention delineated herein.

In another aspect, the compound has the formula (I')

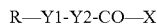
R—Y1-Y2-CO—X where R and X are as hereinbefore defined;
Y1 is selected from O, S, NH, N(C$_{1-6}$-alkyl), SO or SO$_2$ and
Y2 is (CH$_2$)$_n$ or CH(C$_{1-6}$ alkyl); or
Y1 and Y2 taken together form a 5 or 6 membered homo or heterocyclic, optionally unsaturated or aromatic ring; or
Y1 forms a 5 or 6 membered homo or heterocyclic, optionally unsaturated or aromatic ring and Y2 is (CH$_2$)$_n$;
where n is 1, 2, or 3. In one embodiment, n is 1.

In another aspect, the invention provides a compound of formula (I")

R—Y1-Y2-CO—X                                          (I")

wherein R and X are as defined in the above aspect;
Y1 and Y2 taken together form a 5 or 6 membered homo or heterocyclic, optionally unsaturated or aromatic ring; or
Y1 forms a 5 or 6 membered homo or heterocyclic, optionally unsaturated or aromatic ring and Y2 is (CH$_2$)n;
where n is 1, 2, or 3, preferably 1.

In another aspect, the invention provides a compound of formula (II)

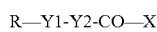
RN(C$_{1-6}$alkyl)(CH$_2$)$_n$COX                                          (II)

where R, n and X are as defined in the previous aspect. In one embodiment, the compound is

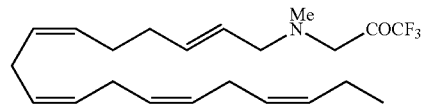

In another aspect, the invention provides a compound of formula (III)

R-L-CO—X                                          (III)

where R and X are as defined in the first aspect, L' represents a linking group forming a bridge of 1 to 5 atoms between the R group and the carbonyl CO, where said L' linking group comprises a ring structure.

In one embodiment, the invention provides a compound as claimed hereinabove of formula (IV) or (V)

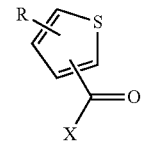

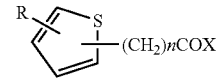

where n is 1 to 3, e.g. 1 to 2.

In another aspect, the invention provides a compound of formula (VI)

RS(C$_{1-6}$alkyl)CH$_2$—COX$^+$Z$^-$ where R and X are as hereinbefore defined and Z is a counterion, e.g. halide; e.g. the compound

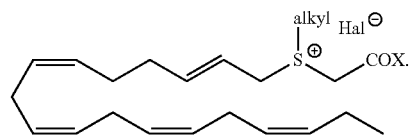

In another aspect, the invention provides a pharmaceutical composition containing an effective amount of a compound delineated herein and at least one pharmaceutically acceptable excipient.

In yet another aspect, the invention provides a process for the preparation of a compound of formula (I) in which the L group contains N comprising:
(I) converting the compound R—OH to R—NH$_2$,
(II) optionally methylating the N atom;
(III) reacting with TFPO; and
(IV) oxidising the formed hydroxyl to a ketone.

Diseases amenable to treatment with a compound delineated herein include, but are not limited to glomerulonephritis, mesangioproliferative glomerulonephritis, nephrotic syndrome, chronic or acute renal failure, proteinuria, hematuria, IgA nephropathy, membranoproliferative glomerulonephritis, lupus nephritis, diabetic nephropathy, and glomerulosclerosis.

By "ameliorate" is meant decrease, suppress, attenuate, diminish, arrest, or stabilize the development or progression of a disease.

By "analog" is meant a molecule that is not identical, but has analogous functional or structural features.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "disease" is meant any condition or disorder that damages or interferes with the normal function of a cell, tissue, or organ.

As used herein, "obtaining" as in "obtaining an agent" includes synthesizing, purchasing, or otherwise acquiring the agent.

By "reference" is meant a standard or control condition.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

In FIG. 2A, supernatants were taken for protein precipitation and precipitated proteins were separated by SDS-PAGE and subjected to a Western blot analysis using a monoclonal antibody against rat $sPLA_2$. Data show duplicates of a representative experiment. In FIG. 2B, cells were taken for RNA extraction and subjected to quantitative PCR analysis of rat IIA-$sPLA_2$ and 18 S RNA. ΔΔCt values were calculated and results are expressed as % of maximal IL-1β-stimulated response and are means+S.D. (n=3). In FIG. 2C, cells were transfected with the sPLA2 promoter construct plus a plasmid coding for the Renilla luciferase. After transfection, cells were stimulated for 24 h with vehicle (−), IL-1β (1 nM), or IL-1β plus 10 μM of AKH-217. sPLA2 promoter activity was calculated and results are expressed as relative luciferase units (RLU) and are means±S.D. (n=3).

In FIG. 4A, cells were taken for protein extraction and equal amount of. protein were separated by SDS-PAGE and subjected to a Western blot analysis using a polyclonal antibody against iNOS at a dilution of 1:2000. Data are representative of at least 3 independent experiments giving similar results. In FIG. 4B, cells were taken for RNA extraction and subjected to quantitative PCR analysis of rat iNOS and 18 S RNA. ΔΔCt values were calculated and results are expressed as % of maximal IL-1β response and are means±S.D (n=3). In FIG. 4C, cells were transfected with the rat iNOS promoter construct plus a plasmid coding for the Renilla luciferase. After transfection, cells were stimulated with vehicle (−), IL-1β (1 nM), or IL-1β plus 10 μM of AVX001. iNOS promoter activity was calculated and results are expressed as relative luciferase units (RLU) and are means±S.D.(n=3).

In FIG. 5A, quiescent cells were stimulated for 24 h with vehicle (DMEM), or 100 μM of ATP in the absence (−) or presence of the indicated concentrations of AVX001 or AVX002, in the presence of [$^3$H]thymidine. In FIG. 5B, cells were stimulated for 24 h with insulin (100 ng/ml) or IGF (50 ng/ml) in the absence (−) or presence of 10 μM of AVX001 or AVX002, in the presence of [$^3$H]thymidine. Thymidine incorporated into DNA was determined and results are expressed as % of control and are means±S.D. (n=3).

In FIG. 6A, quiescent cells were stimulated for 30 min with either vehicle (DMEM), or IL-1β (2 nM) in the absence (−) or presence (+) of AVX001 or AVX002 (10 μM, pretreated 2 h). Thereafter, cell lysates were separated by SDS-PAGE and subjected to a Western blot analysis using a polyclonal antibody against phospho-p65 (NFκB) (upper panel), HuR as a loading control (middle panel), and IκB (lower panel). Data in FIG. 6A show duplicates of one representative experiments. FIGS. 6B and 6C show the densitometric evaluation of NFkB and IkB bands.

DETAILED DESCRIPTION

Figure 1:
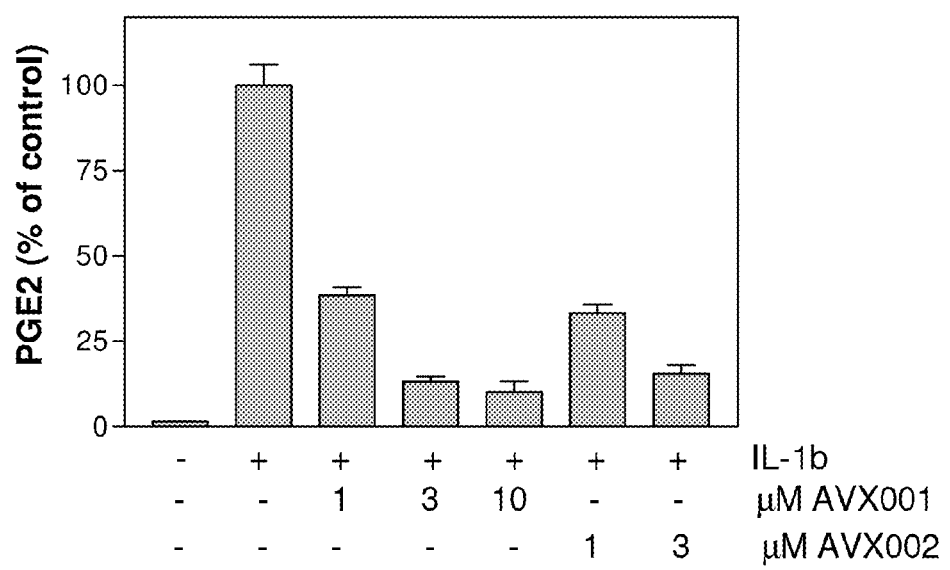
FIG. 1 shows the effect of the inhibitors of the examples on cytokine-stimulated $PGE_2$ formation in mesangial cells. Quiescent cells were stimulated with either DMEM (−), IL-1β (1 nM), in the absence (−) or presence of the indicated concentrations of AKH-217 and AVX002. Supernatants were collected and taken for PGE2 quantification using an ELISA. Data are expressed as % of maximal IL-1β-stimulated PGE2 and are means±S.D. (n=3).

This invention generally provides compositions and methods for the treatment of glomerulonephritis and related conditions (e.g., mesangioproliferative glomerulonephritis, nephrotic syndrome, chronic or acute renal failure, proteinuria, hematuria, IgA nephropathy, membranoproliferative glomerulonephritis, lupus nephritis, diabetic nephropathy, and glomerulosclerosis). More particularly, the invention provides for the use of compounds of formula (I) or a salt thereof in the treatment of glomerulonephritis and related conditions. The invention is based, at least in part, on the discovery that a certain class of compounds based upon long chain unsaturated fatty acid molecules are useful in the treatment of glomerulonephritis.

Glomerulonephritis

Glomerulonephritis is a renal disease characterized by inflammation of the glomeruli. The glomerulus has potential to express several isoforms of nitric oxide synthase (NOS). Induction of inducible NOS occurs as part of a rapid initial response to immune injury in a glomerulonephritis. Whilst the role of NO generated by NOS in the glomerulus is still unclear, some studies have demonstrated that NO inhibition can alter the level of proteinuria and leukocyte infiltration and other manifestations of injury such as thrombosis, proliferation and matrix production.

Current proposed therapies may be based on angiotensin converting enzyme (ACE) inhibitors, such as lisinopril and similar compounds. These inhibitors reduce blood pressure, a feature common to all anti-hypertensive drugs, but they also possess inhibitory activity of intra renal MC proliferation and also lower proteinurea. Other treatments include the use of CDK2 antagonists or calcium antagonists. Reduction of NO may contribute to amelioration of mesangial proliferation and hence offer alleviation of the symptoms of glomerulonephritis.

The present inventors have discovered that the compounds claimed herein, some of which are new, others known, are useful for the treatment of proliferative conditions in general and glomerulonephritis in particular. The inventors have found that a certain class of compounds based upon long chain unsaturated fatty acid molecules are useful in the treatment of glomerulonephritis.

Some of the compounds proposed for use in this invention are described, for example, in EP-A-1469859, which is hereby incorporated by reference in its entirety. EP-A-1469859 describes the use of these compounds in the context of the treatment of psoriasis. The present inventors have realised that these compounds and others also have utility in the treatment of glomerulonephritis or other proliferative diseases.

The group R preferably comprises 5 to 9 double bonds, preferably 5 or 8 double bonds, e.g. 5 to 7 double bonds such as 5 or 6 double bonds. These bonds should be non-conjugated. It is also preferred if the double bonds do not conjugate with the carbonyl functionality.

The double bonds present in the group R may be in the cis or trans configuration however, it is preferred if the majority of the double bonds present (i.e. at least 50%) are in the cis configuration. In further advantageous embodiments all the double bonds in the group R are in the cis configuration or all double bonds are in the cis configuration except the double bond nearest the carbonyl group which may be in the trans configuration.

The group R may have between 10 and 24 carbon atoms, preferably 12 to 20 carbon atoms, especially 17 to 19 carbon atoms.

Whilst the R group can be interrupted by at least one heteroatom or group of heteroatoms, this is not preferred and the R group backbone preferably contains only carbon atoms.

The R group may carry up to three substituents, e.g. selected from halo, $C_{1-6}$ alkyl e.g. methyl, $C_{1-6}$ alkoxy. If present, the substituents are preferably non-polar, and small, e.g. a methyl group. It is preferred however, if the R group remains unsubstituted.

The R group is preferably linear. It preferably derives from a natural source such as a long chain fatty acid or ester. In particular, the R group may derive from AA, EHA or DHA.

The linking group L provides a bridging group of 1 to 5 backbone atoms, preferably 2 to 4 backbone atoms between the R group and the carbonyl. The atoms in the backbone of the linker may be carbon and/or be heteroatoms such as N, O, S, SO, $SO_2$. The atoms can form part of a ring and the backbone atoms of the linking group can be substituted with side chains, e.g. with groups such as $C_{1-6}$ alkyl, oxo, alkoxy, or halo.

Preferred components of the linking group are —$CH_2$—, —CH($C_{1-6}$alkyl)-, —N($C_{1-6}$alkyl)-, —NH—, —S—, —O—, —CH=CH—, —CO—, —SO—, —$SO_2$— which can be combined with each other in any (chemically meaningful) order to form the linking group. Thus, by using two methylene groups and an —S— group the linker —$SCH_2CH_2$— is formed.

It is highly preferred if the linking group L contains at least one heteroatom in the backbone. It is also preferred if the first backbone atom of the linking group attached to the R group is a heteroatom or group of heteroatoms.

It is highly preferred if the linking group L contains at least one —$CH_2$— link in the backbone. Ideally the atoms of the linking group adjacent the carbonyl are —$CH_2$—.

It is preferred that the group R or the group L (depending on the size of the L group) provides a heteroatom or group of heteroatoms positioned α, β, γ, or δ to the carbonyl, preferably β or γ to the carbonyl. Preferably the heteroatom is O, N or S or a sulphur derivative such as SO.

Highly preferred linking groups therefore are —$NH_2CH_2$—, —NH(Me)$CH_2$—, —$SCH_2$—, —$SOCH_2$—, —$COCH_2$—

It is also within the invention for the linking group to be a ring or to comprise a ring. Thus for example, the linker might be thiophene, e.g. 2,4-thiophene which provides a two atom bridge to the carbonyl (via the shortest route). It would also be possible for the linker to be a ring such as furan, tetrahydrofuran, piperidine, cyclohexane, benzene or pyridine. Where the linker comprises a ring it is preferred if this is a 5 or 6 membered ring. It is preferred if the ring comprises at least one heteroatom or group of heteroatoms. It is preferred if the ring is unsaturated or aromatic. When the R and COX groups bind directly to such a ring, it is preferred if the R group and COX group bind on different atoms and preferred if they bind on carbon atoms of the ring.

The substitution pattern is preferably such that the R and carbonyl substituents are alpha, gamma to each other (i.e. 1, 3 or 2, 4 or 3,5-split).

For the avoidance of doubt, it is stressed that the 1 to 5 atom bridge should be counted as the shortest route from the start of the linker to the carbonyl.

Suitable ring linkers are shown below where the R group and carbonyl can bind to any two carbon atoms on these rings:

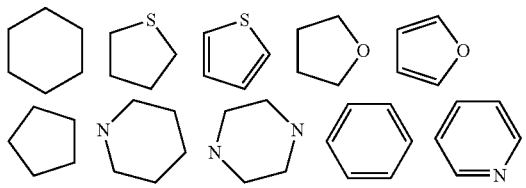

It is also within the scope of the invention for the linker to comprise a ring and non ring portion, e.g. $CH_2$-thiophene or $NH_2$-thiophene and so on. In such a linker it is preferred if the R group binds directly to the ring and that the carbonyl group binds to the non ring portion, e.g. a —$CH_2$— linkage. The skilled man will be able to devise all kinds of different linkers suitable for use in the invention.

Highly preferred linking groups are —$CH_2$—, —$CH_2$—$CH_2$—, —CH(Me), —CH(Me)$CH_2$—, —CH(Me)-CH(Me)-, $SCH_2$, $NHCH_2$, N(Me)$CH_2$, 2,4-thiophene and 2,5-thiophene.

The group X is an electron withdrawing group. Suitable groups in this regard include O—$C_{1-6}$ alkyl, CN, $OCO_2$—$C_{1-6}$ alkyl, phenyl, $CHal_3$, $CHal_2H$, $CHalH_2$ wherein Hal represents a halogen, e.g. fluorine, chlorine, bromine or iodine, preferably fluorine.

In a preferred embodiment the electron withdrawing group is $CHal_3$, especially $CF_3$.

Thus, preferred compounds of formula (I) are those of formula (I')

R—Y1-Y2-CO—X  (I')

wherein R and X are as hereinbefore defined;
Y1 is selected from O, S, NH, N($C_{1-6}$-alkyl), SO or $SO_2$ and
Y2 is $(CH_2)_n$ or CH($C_{1-6}$ alkyl); or
Y1 and Y2 taken together form a 5 or 6 membered homo or heterocyclic, optionally unsaturated or aromatic ring; or
Y1 forms a 5 or 6 membered homo or heterocyclic, optionally unsaturated or aromatic ring and Y2 is $(CH_2)_n$;
where n is 1 to 3, preferably 1.

Highly preferred (known) compounds for use in the invention are depicted below.

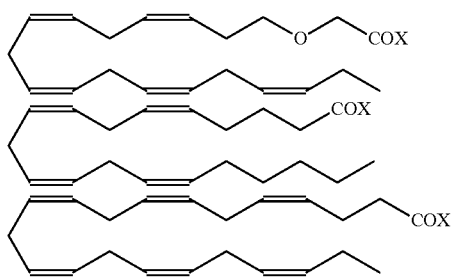
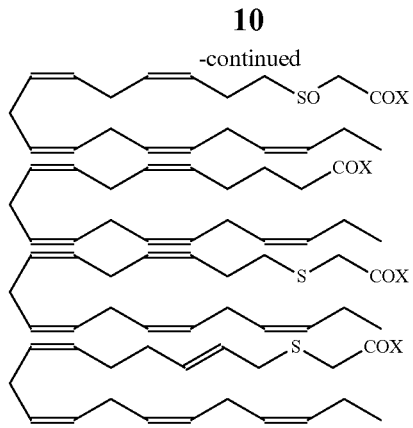

Certain compounds are new and form a further aspect of the invention.

Thus viewed from another aspect the invention provides a compound of formula (I")

R—Y1-Y2-CO—X  (I")

wherein R and X are as hereinbefore defined;
Y1 and Y2 taken together form a 5 or 6 membered homo or heterocyclic, optionally unsaturated or aromatic ring; or
Y1 forms a 5 or 6 membered homo or heterocyclic, optionally unsaturated or aromatic ring and Y2 is $(CH_2)_n$;
where n is 1 to 3, preferably 1.

Further compounds which are new include the compounds RN($C_{1-6}$alkyl)COX. Thus viewed from another aspect the invention provides a compound of formula (II)

RN($C_{1-6}$alkyl)($CH_2$)$_n$COX  (II)

where R, n and X are as hereinbefore defined, especially the compound:

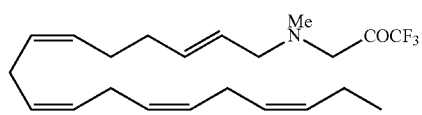

Further preferred compounds which are new are those in which the L group is a ring or comprises a ring. Viewed from another aspect therefore the invention provides a compound of formula (III)

R-L-CO—X  (III)

where R and X are as hereinbefore defined an L' represents a linking group forming a bridge of 1 to 5 atoms between the R group and the carbonyl CO wherein said L' linking group comprises a ring structure.

Preferred compounds of formula (III) are depicted below.

(IV)

(V)

where n is 1 to 3, e.g. 1 to 2.

Especially preferably the groups bind to the 2 and 4 positions of the ring (where atom 1 is the S atom).

Viewed from another aspect the invention provides a pharmaceutical composition comprising any new compound as hereinbefore defined in combination with at least one pharmaceutically acceptable excipient.

The following compounds are highly preferred for use in the invention:

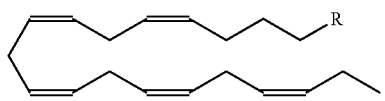

R = COCF$_3$ = EPACOCF$_3$

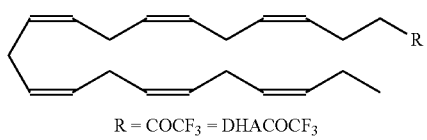

R = COCF$_3$ = DHACOCF$_3$

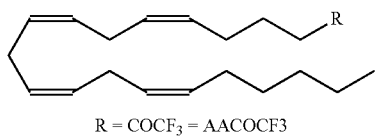

R = COCF$_3$ = AACOCF3

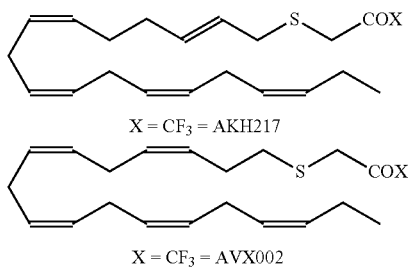

X = CF$_3$ = AKH217

X = CF$_3$ = AVX002

Where possible, the compounds of the invention can be administered in salt, solvate, prodrug or ester form, especially salt form. Preferably however, no such form is used.

Typically, a pharmaceutical acceptable salt may be readily prepared by using a desired acid. The salt may precipitate from solution and be collected by filtration or may be recovered by evaporation of the solvent. For example, an aqueous solution of an acid such as hydrochloric acid may be added to an aqueous suspension of a compound of formula (I) and the resulting mixture evaporated to dryness (lyophilised) to obtain the acid addition salt as a solid. Alternatively, a compound of formula (I) may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Suitable addition salts are formed from inorganic or organic acids which form non-toxic salts and examples are hydrochloride, hydrobromide, hydroiodide, sulphate, bisulphate, nitrate, phosphate, hydrogen phosphate, acetate, trifluoroacetate, maleate, malate, fumarate, lactate, tartrate, citrate, formate, gluconate, succinate, pyruvate, oxalate, oxaloacetate, trifluoroacetate, saccharate, benzoate, alkyl or aryl sulphonates (eg methanesulphonate, ethanesulphonate, benzenesulphonate or p-toluenesulphonate) and isethionate. Representative examples include trifluoroacetate and formate salts, for example the bis or tris trifluoroacetate salts and the mono or diformate salts, in particular the tris or bis trifluoroacetate salt and the monoformate salt.

In a further highly preferred embodiment, the compound of the invention is a sulphonium salt. In such a compound, a sulphur atom in the backbone of the molecule, e.g. in the linker group, is functionalised to carry a C1-6-alkyl group. This can be achieved through reaction with an alkyl halide, e.g. methyl iodide. The halide ion forms the counterion of the salt.

In a further preferred embodiment therefore the invention provides a sulphonium salt of a compound of formula (I). Preferably the compound is of formula (VI)

$$RS(C_{1-6}alkyl)CH_2{-}COX^+Z^- \qquad (VI)$$

where R and X are as hereinbefore defined and Z is a counterion, e.g. halide; e.g. the compound

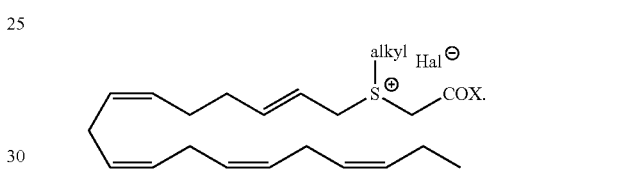

Compounds of formula (I) may be manufactured using known chemical synthetic routes. It is convenient to begin synthesis from the commercially available compounds arachidonic acid (AA), EPA (all-Z-eicosa-5,8,11,14,17-pentaenoic acid) or DHA (all-Z-docosa-4,7,10,13,16,19-hexaenoic acid). Conversion of the acid functionality of these compounds into, for example a —COCF$_3$ group can be achieved readily, e.g. by converting the carboxylic acid into its corresponding acid chloride and reacting the same with trifluoroacetic anhydride in the presence of pyridine.

Introduction of a heteroatom into the carbon chain is also achieved readily. Conveniently, for example, the starting acid is reduced to an alcohol and, if required, converted to the corresponding thiol. The nucleophilic thiol may then be reacted with a group such as BrCH$_2$COCF$_3$ thereby introducing the carbonyl and electron withdrawing species. Complete synthetic protocols may be found in J. Chem. Soc., Perkin Trans 1, 2000, 2271-2276 or J. Immunol., 1998, 161, 3421.

Where the backbone of the molecule contains a nitrogen atom, an alternative synthesis is required. Formation of a polyunsaturated alcohol can be achieved using protocols give in the above Perkin Trans paper. Thereafter, conversion of an alcohol —OH to —NH$_2$ with, for example, phthalimide and subsequent hydrazine reduction allows formation of a —NH$_2$CH$_2$COCF$_3$ group by reaction with trifluoropropyleneoxide (TFPO) and oxidation of the hydroxyl to a ketone. This reaction is shown below.

Methylation of the nitrogen can be effected before this reaction by the formation of an N—BOC group and reduction, e.g. with lithium aluminium hydride. Reaction with TFPO and oxidation yields the linker NMe-CH$_2$.

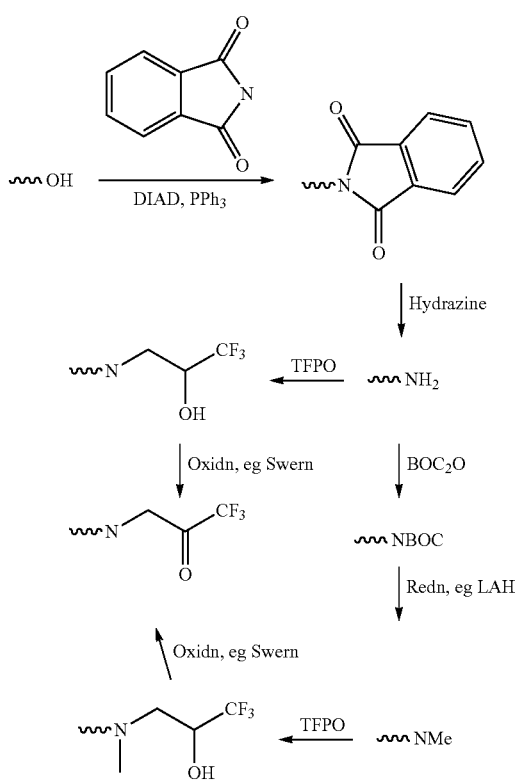

This forms a further aspect of the invention which therefore provides a process for the preparation of a compound of formula (I) comprising:
(I) converting the compound R—OH to R—NH$_2$,
(II) optionally methylating the N atom;
(III) reacting with TFPO; and
(IV) oxidising the formed hydroxyl to a ketone.

The compounds of the invention are proposed primarily for use in the treatment of, inter alia, glomerulonephritis. Whilst the compounds of the invention are generally of use in the treatment of glomerulonephritis, the compounds are of particular utility in the treatment of a proliferative type of disease.

By treating or treatment is meant at least one of:
(i). preventing or delaying the appearance of clinical symptoms of the disease developing in a mammal;
(ii). inhibiting the disease i.e. arresting, reducing or delaying the development of the disease or a relapse thereof or at least one clinical or subclinical symptom thereof, or
(iii). relieving or attenuating one or more of the clinical or subclinical symptoms of the disease.

The benefit to a subject to be treated is either statistically significant or at least perceptible to the patient or to the physician. In general a skilled man can appreciate when "treatment" occurs.

The word "treatment" is also used herein to cover prophylactic treatment, i.e. treating subjects who are at risk of developing a disease in question.

The compounds of the invention can be used on any animal subject, in particular a mammal and more particularly to a human or an animal serving as a model for a disease (e.g., mouse, monkey, etc.).

In order to treat a disease an effective amount of the active agent needs to be administered to a patient. A "therapeutically effective amount" means the amount of a compound that, when administered to an animal for treating a state, disorder or condition, is sufficient to effect such treatment. The "therapeutically effective amount" will vary depending on the compound, the disease and its severity and the age, weight, physical condition and responsiveness of the subject to be treated and will be ultimately at the discretion of the attendant doctor.

While it is possible that, for use in the methods of the invention, a compound of formula I may be administered as the bulk substance, it is preferable to present the active ingredient in a pharmaceutical formulation, for example, wherein the agent is in admixture with a pharmaceutically acceptable carrier selected with regard to the intended route of administration and standard pharmaceutical practice.

The term "carrier" refers to a diluent, excipient, and/or vehicle with which an active compound is administered. The pharmaceutical compositions of the invention may contain combinations of more than one carrier. Such pharmaceutical carriers are well known in the art. The pharmaceutical compositions may also comprise any suitable binder(s), lubricant(s), suspending agent(s), coating agent(s), and/or solubilizing agent(s) and so on. The compositions can also contain other active components, e.g. other drugs for the treatment of glomerulonephritis.

It will be appreciated that pharmaceutical compositions for use in accordance with the present invention may be in the form of oral, parenteral, transdermal, inhalation, sublingual, topical, implant, nasal, or enterally administered (or other mucosally administered) suspensions, capsules or tablets, which may be formulated in conventional manner using one or more pharmaceutically acceptable carriers or excipients. The compositions of the invention could also be formulated as nanoparticle formulations.

The compounds of the invention can be administered for immediate-, delayed-, modified-, sustained-, pulsed- or controlled-release applications.

The pharmaceutical compositions of the invention may contain from 0.01 to 99% weight-per volume of the active material.

A therapeutically effective amount of the compound of the present invention can be determined by methods known in the art. The therapeutically effective quantities will depend on the age and on the general physiological condition of the patient, the route of administration and the pharmaceutical formulation used. The therapeutic doses will generally be between about 10 and 2000 mg/day and preferably between about 30 and 1500 mg/day. Other ranges may be used, including, for example, 50-500 mg/day, 50-300 mg/day, 100-200 mg/day.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art.

It is advantageous if the medicament of the invention is taken orally.

The compounds of the invention may be used in the treatment of glomerulonephritis and related diseases. In particular, the compounds of the invention may be used to treat mesangioproliferative glomerulonephritis, nephrotic syndrome, chronic or acute renal failure, proteinuria, hematuria, IgA nephropathy, glomerulonephritis, lupus nephritis, diabetic nephropathy, and glomerulosclerosis.

The compounds of the invention may be used to treat glomerulonephritis in combination with other known pharmaceuticals for said purpose and this forms a further aspect of the invention. Other useful pharmaceuticals include corticosteriods, immunosuppressive drugs, antihypertensive agents and diuretic medications.

Accordingly, the present invention provides methods of treating disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to glomerulonephritis and related diseases including, but not limited to mesangioproliferative glomerulonephritis, nephrotic syndrome, chronic or acute renal failure, proteinuria, hematuria, IgA nephropathy, membranoproliferative glomerulonephritis, lupus nephritis, diabetic nephropathy, and glomeruloscerlosis, as well as proliferatives diseases or disorders or symptoms thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which proliferation may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with glomerulonephritis and related diseases, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

The invention is described further below with reference-to the following non-limiting examples and figures.

EXAMPLES

The following compounds were used in the Experiments:

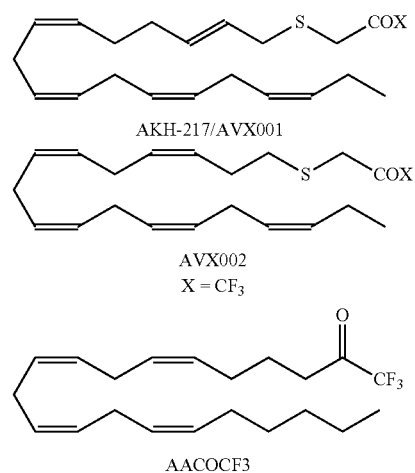

These compounds were synthesised based on. Chem. Soc., Perkin Trans 1, 2000, 2271-2276, which is incorporated by reference in its entirety.

Example 1

Effect of Inhibitors on PGE2 Formation in Rat Renal Mesangial Cells

We investigated the effect of the inhibitors on PGE2 formation in mesangial cells. PGE2 formation is highly induced by stimulation of cells with the pro-inflammatory cytokine IL-1β. This induction of PGE2 is dose-dependently reduced in the presence of the inhibitors. Maximal effects were seen with 3-10 μM of AKH-217 (AVX001) and Compound B (AVX002) (FIG. 1).

Figure 2:
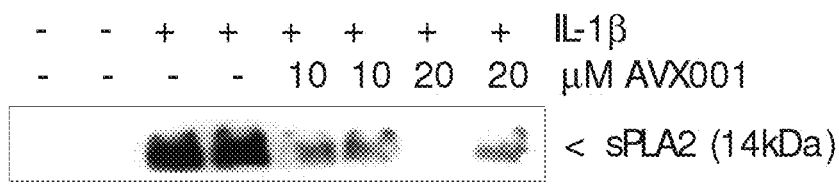
FIGS. 2A to 2C show the effect of the inhibitors of the examples on cytokine-stimulated $sPLA_2$ protein (FIG. 2A) and mRNA (FIG. 2B) expression and promoter activity in mesangial cells. Quiescent cells were stimulated with either DMEM (−), or IL-1β (1 nM) in the absence (−) or presence of AKH-217 (etOH), vehicle control.
Figure 2:
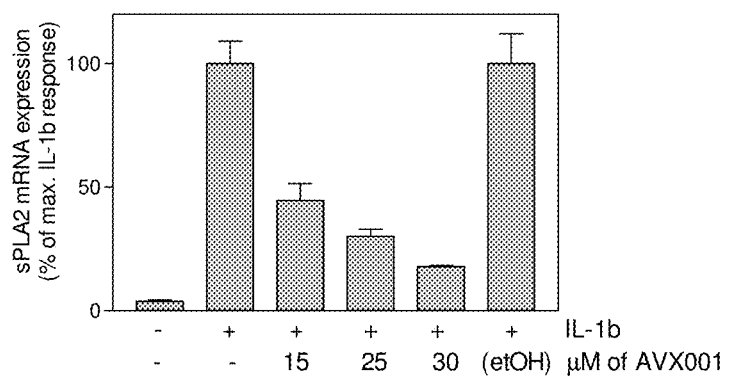
Figure 2:
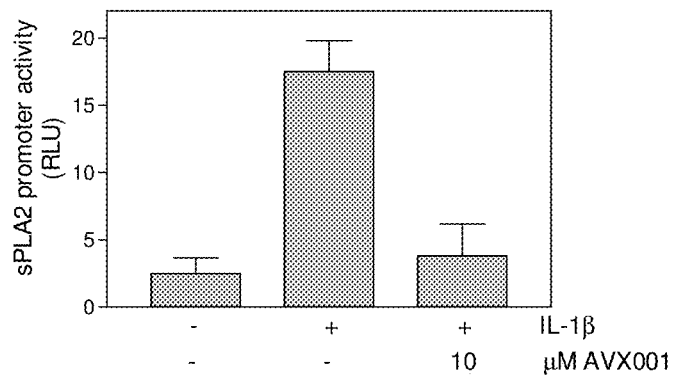

It has been previously shown that the cytokine-induced PGE2 formation in mesangial cells involves both sPLA2 and cPLA2 activation (Pfeilschifter et al., 1993), we then investigated the effect of the inhibitors above on sPLA2 protein and mRNA expressions. As seen in FIG. 2, AKH-217 was able to reduce the IIA-sPLA2 protein expression and secretion (FIG. 2A), but also IIA-sPLA2 mRNA expression (FIG. 2B). This effect on sPLA2 mRNA expression was due to a reducing effect on gene transcription. This was shown by a luciferase reporter gene assay that reflected sPLA2 promoter activity.

To this end, a 2.26 kb fragment of the rat IIA-sPLA2 promoter was cloned according to Scholz-Pedretti et al. (2002). This fragment was ligated into a luciferase-containing vector (pGL3) and used to transfect mesangial cells. As seen in FIG. 2C, the IL-1β-stimulated promoter activity was completely reduced by AKH-217.

These data indicate that the inhibitors of the invention could affect some transcription factors, which are activated by IL-1β and are essential for sPLA2 gene transcription. Potential candidates include NFkB and PPAR.

Example 2

Effect of Inhibitors on Nitric Oxide (NO) Formation in Rat Renal Mesangial Cells Nitric oxide (NO) is also considered a pro-inflammatory mediator which is generated by the inducible NO synthase (iNOS) upon cytokine treatment of mesangial cells. Various previous studies have indicated that iNOS expression is regulated by the same transcription factors as sPLA2. We investigated whether cytokine-triggered iNOS expression is also affected by the inhibitors.

Figure 3:
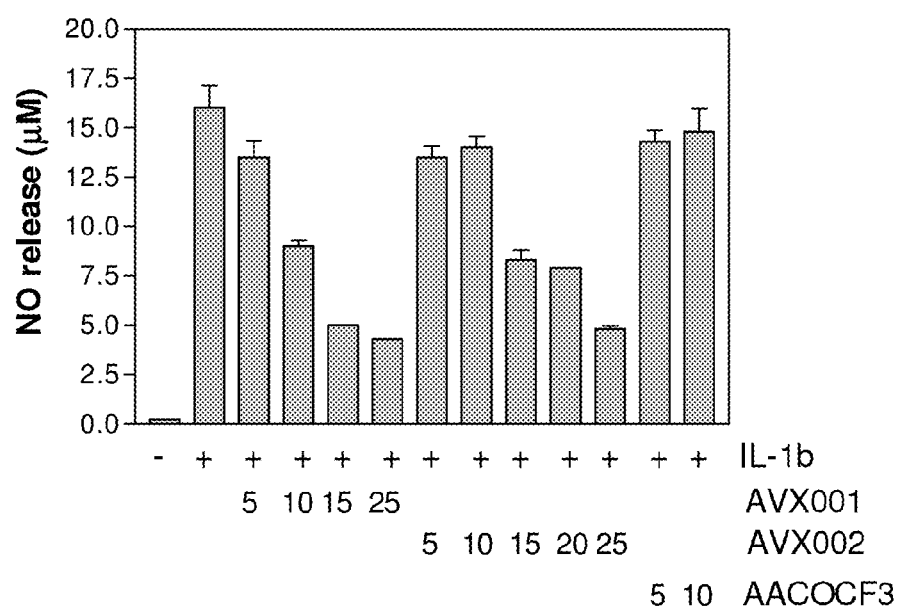
FIG. 3 shows the effect of the inhibitors of the examples on cytokine-stimulated NO formation in mesangial cells. Quiescent cells were stimulated with either DMEM (−), IL-1β (1 nM; +), in the absence or presence of the indicated concentrations of AKH-217, AVX002, or AACOCF3. Supernatants were collected and taken for nitric oxide (NO) quantification by using a Griess Reaction assay. Data are expressed as μM of NO in the supernatant and are means±S.D. (n=3).
Figure 4:
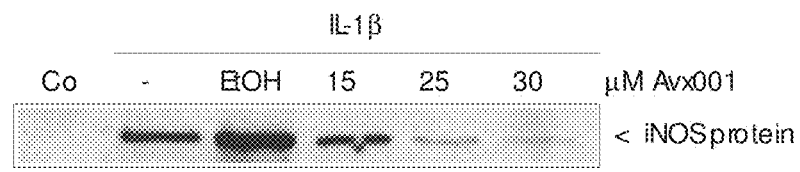
FIGS. 4A to 4C show the effect of the inhibitors of the examples on cytokine-stimulated iNOS protein (FIG. 4A) and mRNA (FIG. 4B) expression and promoter activity in mesangiai cells. Quiescent cells were stimulated with either vehicle (DMEM), IL-1β (1 nM), in the absence (−) or presence of the indicated concentrations (in μM) of AVX001 and AVX002. EtOH, vehicle control.
Figure 4:
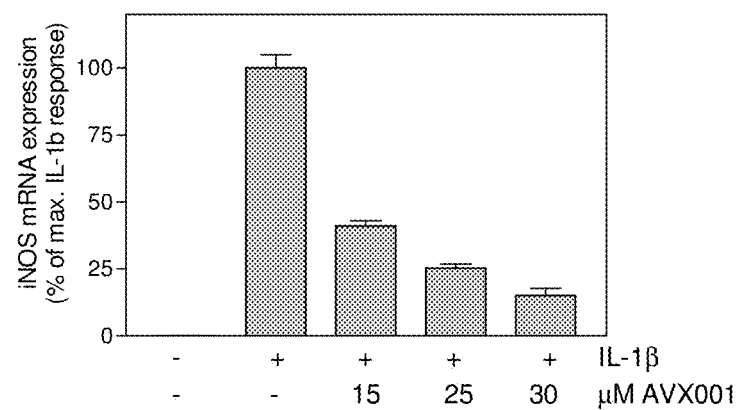
Figure 4:
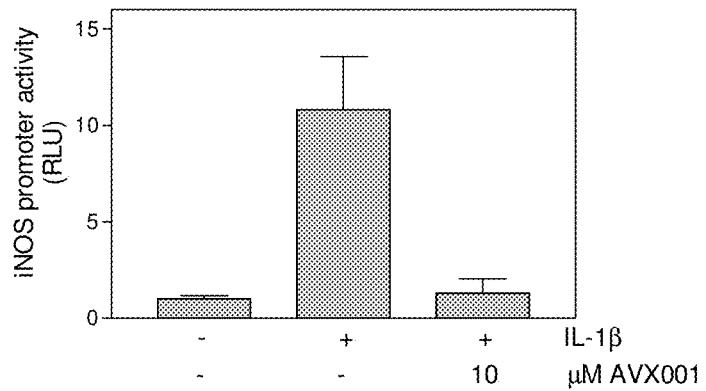

NO formation in mesangial cells was highly induced by IL-1 β treatment. This stimulated NO formation was reduced in a dose-dependent manner in the presence of AKH-217 and AVX002 (FIG. 3). Furthermore, the protein expression of iNOS, which is induced by IL-1 β (FIG. 4A), is down-regulated in the presence of AKH-217 and AVX002 (FIG. 4A). A similar reducing effect was also seen on iNOS mRNA expression when quantitative RealTime PCR analyses were performed (FIG. 4B). To see whether this effect is due to altered gene transcription of iNOS, luciferase reporter gene assays were performed to measure iNOS promoter activity. A 4.5 kb fragment of the rat iNOS promoter was kindly provided by Dr. K. F. Beck (pharmazentrum frankfurt). As seen in FIG. 4C, IL-1 β stimulation of mesangial cells stimulated iNOS promoter by 10-fold. In the presence of AKH217, the promoter activity was completely lost.

These data indicate that also in the case of iNOS, AVX inhibitors have a reducing effect on gene transcription, most probably affecting the same transcription factors as in the case of sPLA2 transcription.

Example 3

Effect of Inhibitors on Mesangial Cell Proliferation

Figure 5:
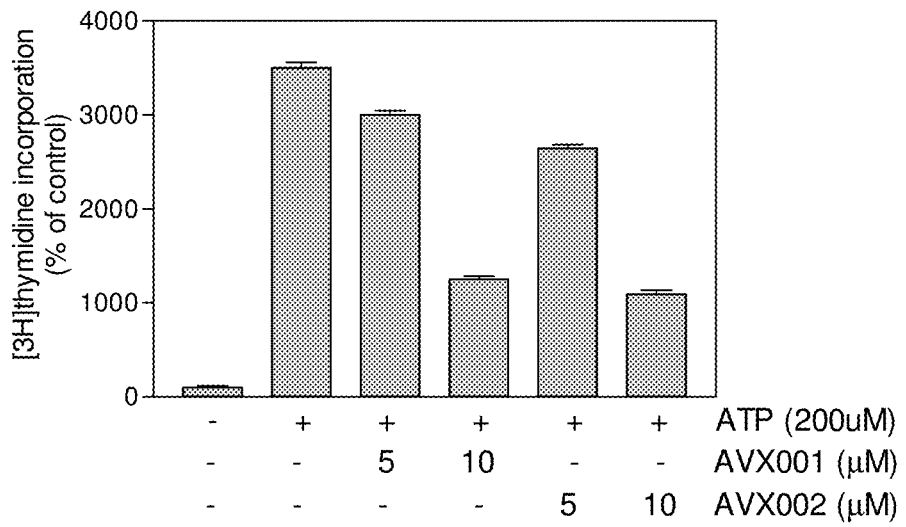
FIGS. 5A and 5B show the effect of the inhibitors of the examples on [$^3$H]thymidine incorporation in mesangial cells.
Figure 5:
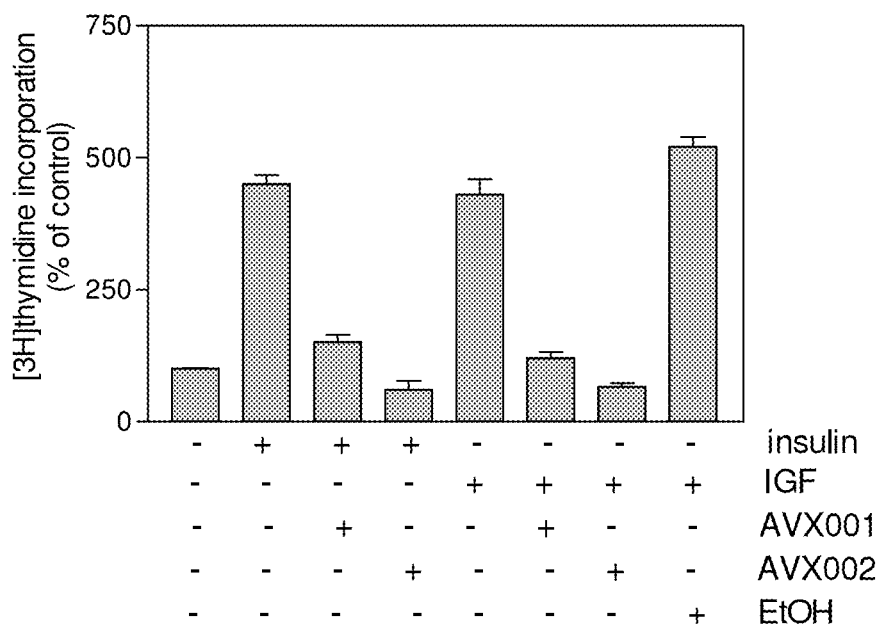

Glomerulonephritis is characterized in a first early phase by increased mesangial apoptosis which in a second phase is replaced by an opposite event, i.e. hyperproliferation of mesangial cells. Many previous studies have shown that quiescent mesangial cells in culture can re-enter the cell cycle when exposed to various growth factors, including PDGF, insulin, insulin-like growth factor (IGF), or extracellular nucleotides such as ATP and UTP. These data are confirmed here, as insulin, IGF and ATP trigger increased [$^3$H]thymidine incorporation into DNA (FIGS. 5A and 5B). In the presence of either AKH217 or AVX002, agonist-stimulated [$^3$H]thymidine incorporation is reduced (FIGS. 5A and 5B). Similar data were also obtained when cells were stimulated with PDGF. These data suggest an anti-proliferative potential of the inhibitors.

Example 4

Effect of Inhibitors on NFkB Activity in Mesangial Cells

Figure 6:
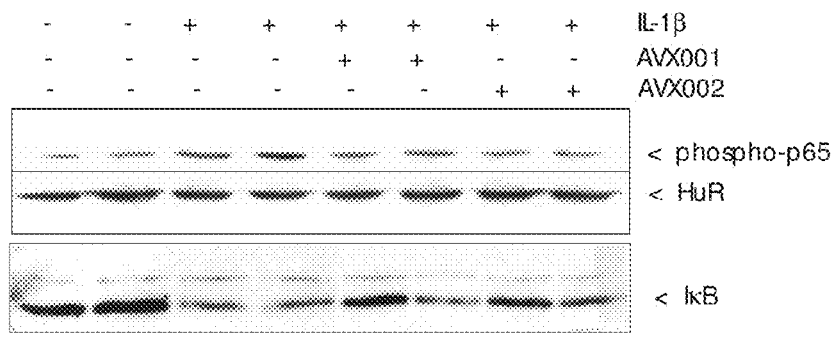
FIGS. 6A to 6C show the effect of the inhibitors of the examples on IL-1β-stimulated NFκB activation in mesangial cells.
Figure 6:
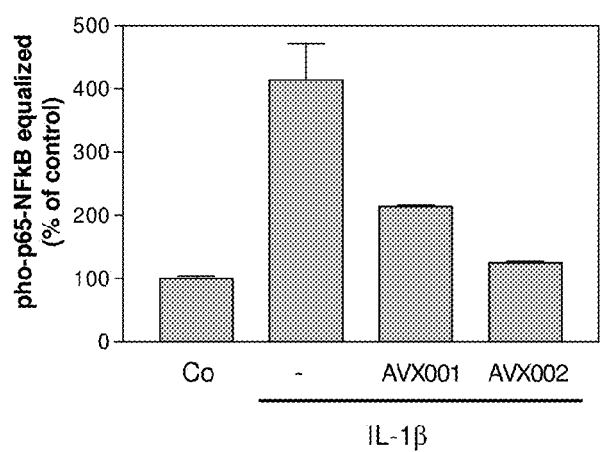
Figure 6:
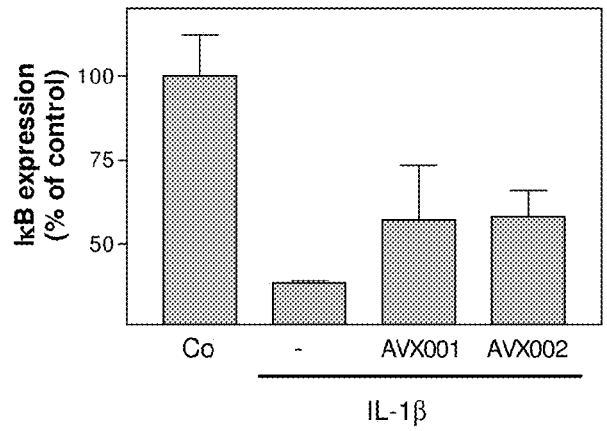

As we have seen in Examples 1 and 2, that iNOS and sPLA2 expression is regulated by the inhibitors in a similar manner, we further studied whether these inhibitors had an effect on NFkB activation. NFkB activation was measured by Western blot analyses by detecting the amount of phospho-p65 which represents the active transcription factor subunit. Short-term stimulation of cells with IL-1β (3 revealed a small but clear increase of phospho-p65 (FIG. 6, upper panel) consistent with many previous reports that cytokines activate NFkB. This effect was reduced by AKH217 (FIG. 6). In addition, the inhibitor of kB (IkB), which is constitutively expressed in unstimulated cells, is downregulated by IL-1 β stimulation, and this downregulation is reverted by the inhibitors (FIG. 6, lower panel). For equal loading, the nuclear HuR stabilization factor was stained (FIG. 6, middle panel).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The invention claimed is:

1. A method of treating lupus nephritis or diabetic nephropathy comprising administering to an animal in need thereof an effective amount of a compound selected from the group consisting of

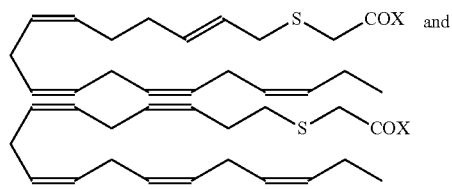
where X is CF$_3$.
2. The method of claim 1, wherein the animal is a mammal.
3. The method of claim 1, wherein the animal is human.
* * * * *